United States Patent [19]

Aeschbach et al.

[11] Patent Number: 5,256,700
[45] Date of Patent: Oct. 26, 1993

[54] CARNOSIC ACID OBTENTION AND USES

[75] Inventors: Robert Aeschbach, Vevey; Georges Philippossian, Lausanne, both of Switzerland

[73] Assignee: Nestec S.A., Vevey, Switzerland

[21] Appl. No.: 761,669

[22] Filed: Sep. 18, 1991

[30] Foreign Application Priority Data

Oct. 6, 1990 [EP] European Pat. Off. ........ 90119218.7

[51] Int. Cl.$^5$ ............................................. A61K 31/05
[52] U.S. Cl. ..................................... 514/732; 514/934
[58] Field of Search ................. 514/732'934; 568/326; 562/466, 475

[56] References Cited

U.S. PATENT DOCUMENTS

| | | | |
|---|---|---|---|
| 4,450,097 | 5/1984 | Nakatani et al. | 252/404 |
| 4,638,095 | 1/1987 | Chang et al. | 568/326 |
| 5,102,659 | 4/1992 | Hudson | 424/195.1 |

OTHER PUBLICATIONS

Linde, "Ein neues Diterpen aus Salvia officinalis L. und eine Notiz zur Konstitution von Pikrosalvin", *Helv. Chim. Acta.* 47, No. 136, 1234 (1964) [p. 1, 1. 21].
Wenkert, et al., "Chemical Artifacts from the Family Labiatae", *J. Org. Chem.* 30, 2931 (1965) [p. 1, 1. 22].
Savona, et al., "Terpenoids of Cultivated Salvia Canariensis", *J. Nat. Prod.* 46, No. 2, 593 (1983) [p. 1, 1. 24].
de La Torre, et al., "Terpenoids From Salvia Willeana and S. Virgata", *Phytochemistry* 29, 668 (1990) [p. 1, 1. 25].
Brieskorn, et al., "Carnosolsäure, der wichtige antioxydativ wirksame Inhaltsstoff des Rosmarin- und Salbeiblattes", *Z. Lebensm. Unters. Forsch.* 141, 10 (1969) [p. 1, 1. 28].
Chemical Abstracts–Carnosic Acid and Derivatives: (a) 86, 117603r, (1976); (b) 90, 49011b, (1978); (c) 97, 67513r, (1981); (d) 97, 69163a, (1981); (e) 97, 69164b, (1981); (f) 104, 221930w, (1986); (g) 111, 130594t (1989); (h) 97, 84835q (1982) [p. 1, 1s. 32–35].
Public Database Abstract Japanese Patent Application 59 103 665 [p.2, 1. 2].
Brieskorn, et al., "Die Struktur des Pikrosalvins, eines Diterpen-o-diphenol-lactons aus dem Salbeiblatt", *Chem. Ber.* 95, 3034 (1962) [p. 2, 1. 12].
Brieskorn, et al., "The Structure of Carnosol", *J. Org. Chem.* 29, 2293 (1964) [p.2, 1. 13].
Inatani, et al., "Structure of a New Antioxidative Phenolic Diterpene Isolated from Rosemary (Rosmarinus officinalis L.).", *Agric. Biol. Chem.* 46(6) 1661 (1982) [p. 2, 1. 14].
Houlihan, et al., "Elucidation of the Chemical Structure of a Novel Antioxidant, Rosmaridiphenol, Isolated from Rosemary", *J. Am. Oil Chem. Soc.* 61, 1036 (1984) [p. 2, 1. 15].
Meyer, et al., "Diterpenoid Total Synthesis, An A→B→C Approach. III. Total Synthesis of Ethyl dl–Carnosate Dimethyl Ether", *Tetrahedron Letters*, No. 36, pp. 4261 (1966) [p. 3, 1. 19].
Shew, et al., "Diterpenoid Total Synthesis, An A→B→C Approach V. Total Synthesis of dl-Carnosol Dimethyl Ether and dl-Carnosic Acid Dimethyl Ether", *Tetrahedron Letters*, No. 25, p. 2963 (1968) [p. 3, 1. 20].
Meyer, et al., "Diterpenoid Total Synthesis, an A→B→C Approach. VIII. Introduction of Oxygen at Carbon-11. Total Synthesis of (±)-Cernosic Acid Dimethyl Ether$^1$ and (±)-Carnosol Dimethyl Ether$^{1}$", *J. Org. Chem.*, vol. 41, No. 6, (1976) [p. 3, 1. 20].
Brieskorn, et al., "Natürliche und synthetische Derivate der Carnosolsäure.", *Arch. Pharm.* 302, 641 (1969) [p.3, 1.29].
European Search Report.
Chemical Abstracts: 88, 69046d, (1978).
Dentali, et al., "16-Hydroxycarnosic Acid, A Diterpene From Salvia Apiana", *Phytochem.*, vol. 29, No. 3, 993, (1990).

*Primary Examiner*—John W. Rollins
*Attorney, Agent, or Firm*—Vogt & O'Donnell

[57] ABSTRACT

Carnosic acid is obtained by extracting sage and rosemary with an apolar solvent, contacting the extract with an adsorbent material to separate carnosic acid from apolar compounds of the extract, desorbing the adsorbent with a polar solvent and then evaporating the solvent to obtain a residue containing carnosic acid. The carnosic acid contained in the residue may be purified by crystallizing it from the residue.

21 Claims, No Drawings

CARNOSIC ACID OBTENTION AND USES

BACKGROUND OF THE INVENTION

This invention relates to a process for the preparation of carnosic acid from rosemary or sage. The invention also relates to the use of carnosic acid for its anticarcinogenic and antiviral properties.

Carnosic acid is a phenolic diterpene which corresponds to the empirical formula $C_{20}H_{28}O_4$ and which has the following structure

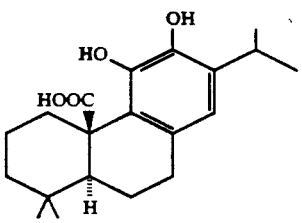

I

It is a constituent of the species Salvia and Rosmarinus where it is mainly to be found in the leaves. It was discovered for the first time by Linde in *Salvia officinalis* [Helv. Chim Acta 47, 1234 (1962)] and by Wenkert et al. in *Rosmarinus officinalis* [J. Org. Chem. 30, 2931 (1965)]. It was then positively identified in various other species of sage, such as for example *Salvia canariensis* [Savona and Bruno, J. Nat. Prod. 46, 594 (1983)] or *Salvia willeana* [de la Torre et al., Phytochemistry 29, 668 (1990)]. It is also present in Salvia triloba and Salvia sclarea.

Carnosic acid is a powerful antioxidant [Brieskorn and Dömling, Z. Lebensm. Unters. Forsch. 141, 10 (1969)] and, according to a number of Russian works where it bears the name salvine, an antibiotic against Staphylococcus aureus [CA 86, 117603r; 90, 49011b; 97, 67513r, 69163a, 69164b; 104, 221930w; 111, 130594t] and against certain microorganisms responsible for dental caries and bad breath [CA 97, 84835q]. In connection with this latter property, it is mentioned in the prior art for the production of dentifrices and mouthwashes [JP 59 103 665, Lion Corp.].

Despite this large of number of references, the isolation on a preparative scale of carnosic acid from rosemary or sage has never been described either by Linde or Wenkert, where its existence is indirectly proved, or by those whose subsequently identified it in various species of sage.

By contrast, many other phenolic diterpenes similar in structure to carnosic acid have been isolated from one or other of the two species Salvia and Rosmarinus. They include carnosol [Brieskorn et al., Chem. Ber. 95, 3034 (1962); J. Org. Chem. 29, 2293 (1964)] and, more recently, rosmanol [Inatani et al., Agric. Biol. Chem. 46, 1661 (1982)] or rosmaridiphenol [Houlihan et al., J. Am. Oil Chem. Soc. 61, 1036 (1984)], the last two having been patented as new antioxidant principles of rosemary U.S. Pat. No. 4,450,097, Nakatani et al., Lion Corp., Tokyo; U.S. Pat. No. 4,638,095, Chang et al., Research Corp., N.Y.].

Although all these compounds are worthy of interest as antioxidants, it nevertheless remains that, compared with carnosic acid, they have certain unfavourable features. Their content in rosemary or sage is much lower than that of carnosic acid.

Dried leaves of rosemary or sage (species Salvia officinalis) contain between 1.5 and 2.5% carnosic acid and only about 0.3-0.4% carnosol. Rosmanol and rosmaridiphenol are present in undetectable concentrations. Accordingly, from the point of view of the economy of a production process, carnosic acid has an indisputable advantage. According to the data disclosed in U.S. Pat. No. 4,450,097 for example, it may be calculated that the yield of rosmanol isolated from rosemary is only 0.01%.

As was demonstrated by Wenkert et al., carnosol is an oxidative artefact of carnosic acid. This oxidation takes place in the presence of oxygen both after the harvesting of rosemary or sage in the leaves left to dry in air (it can incidentally be demonstrated that the freshly cut leaves of rosemary do not contain carnosol) and when the leaves are subjected to extraction with solvents or when the extracts themselves are subjected to conventional operations of fractionation, enrichment and purification. There is every reason to assume that rosmanol, which has been identified in a rosemary fraction subjected to an alkaline treatment, is itself a subsequent product of the oxidation of carnosic acid, as Wenkert et al. already suggested; the same may also be reasonably assumed of rosmaridiphenol. Carnosic acid is therefore the only phenolic diterpene present in the native state in rosemary and sage and, accordingly, has the sole right to be called a natural product.

Some methods for the preparation of carnosic acid by chemical synthesis have also been proposed in the literature by W. L. Meyer et al. [Tetrahedron Letters 1966, 4261; 1968, 2963; J. Org. Chem. 41, 1005 (1976)]. However, the syntheses involved are long and complex and, for economic reasons, cannot be applied to an industrial process. In addition, these syntheses lead to racemic mixtures of carnosic acid precursors and not to the pure enantiomers. It should also be pointed out that these works stop at the preparation of carnosic acid precursors and omit to describe the final preparation step(s). Another method of obtaining carnosic acid has been described in the literature by Brieskorn and Dömling [Arch. Pharm. 302, 641 (1969)], comprising the catalytic reduction of carnosol. Once again, the application of this process on a large scale could not be envisaged on account of the non-availability of carnosol.

SUMMARY OF THE INVENTION

The problem addressed by the present invention was to provide a process for the extraction of carnosic acid from rosemary or sage which would be economical, workable on an industrial scale and would enable pure carnosic acid to be obtained in a high yield.

The present invention relates to a process for the obtained of carnosic acid from rosemary or sage, in which the spice is extracted with an apolar solvent or mixture of highly apolar solvents, the extract obtained is subjected to a selective adsorption treatment on a solid support, the carnosic acid is desorbed with a polar solvent or with a mixture of polar solvents and the solvent is evaporated.

Carnosic acid, like any molecule of the catechol (ortho-diphenol) type, is a reactive compound which is highly sensitive to oxidation and, hence, to all the operations typically carried out to isolate natural substances (extraction, liquid-liquid separation, chromatographic fractionation, etc.). By contrast, it has been found that, in its purified and crystallized form, carnosic acid is stable and can be handled without excessive precautions, although its production in crystallized form can only be carried out from a preparation of vegetable material already enriched with carnosic acid.

The process according to the present invention enables the chemical integrity of carnosic acid to be preserved because it only comprises two treatment steps which are sparing of the basic product and which are selective with respect to the carnosic acid.

The process according to the present invention utilizes two physico-chemical properties of carnosic acid. On the one hand, the molecule comprises reputedly polar functions, such as the carboxylic acid and phenol function. On the other hand, the remainder of its skeleton, made up essentially of hydrocarbons, provides a relatively apolar character by comparison with all other phenolic compounds, such as the flavonoids or hydroxybenzoic or hydroxycinnamic acids which are present in abundance in plants such as sage or rosemary. Thus, the process comprises only two steps, namely:

1. Extraction of the vegetable material (sage or rosemary) in an apolar solvent, so that the carnosic acid and the apolar compounds of the vegetable material enter the extract;
2. Selective adsorption of the carnosic acid present in the extract onto a solid support selected for its affinity, and for its selectivity with respect to the polar functions of carnosic acid, followed by desorption of the carnosic acid from the support with a polar solvent.

DETAILED DESCRIPTION OF THE INVENTION

In the first step of the present invention, leaves of rosemary or sage are extracted with an apolar solvent so that, besides all the other apolar or substantially apolar compounds in the leaves of these plants, such as the components of the essential oil, lipids, waxes, chlorophyll-containing pigments and certain triterpenes, the extract obtained contains carnosic acid as virtually the only phenolic compound entering the extract. The degree of extraction of the carnosic acid is between 70 and 100% while its content in the extract is between 13 and 25%.

In the second step, the extract obtained in the first step is treated by contacting it with an adsorbent solid material which has an affinity for the compounds containing polar functions or a particular affinity with respect to phenolic compounds, such as for example silica gel, aluminium oxide as inorganic absorbent materials or polyamide, polyvinyl pyrrolidone as examples of organic absorbent materials. During this treatment, the carnosic acid is adsorbed with a high affinity or selectivity on the adsorbent, the other constituents of the extract essentially remaining in the liquid phase. After removal of the liquid phase, the carnosic acid is desorbed from the adsorbent by contact with a polar solvent which, after evaporation, gives a residue containing between 65 and 95% carnosic acid which, if necessary, may be further purified by crystallization.

The yield of carnosic acid in the process according to the invention, based on the content of this acid in the vegetable starting material, is between 60 and 90%.

The vegetable starting material and the size of the vegetable particles play a part in the extraction yield of the carnosic acid. In principle, it is preferred to use finely ground rosemary or sage, fine grinding generally giving better yields. Although it is of greater advantage to start from the whole spice, the residues obtained after distillation of the essential oil with water may also be used although it is pointed out that, since this operation is accompanied by significant losses of carnosic acid in the form of its oxidation product, the process for obtaining carnosic acid would be economically less favourable. The residues obtained after extraction of the essential oil with a solvent in the supercritical phase, such as supercritical $CO_2$ for example, may also be used as starting material. In this case, the residues will be of better quality from the point of view of their carnosic acid content because this method of obtaining the essential oil provides for better management the valuable compounds of the vegetable material.

Generally, carnosic acid can be extracted more easily from sage than from rosemary. The reason for this is undoubtedly the fact that the sage leaves are less fibrous than the rosemary leaves. However, rosemary is far more widespread than sage and therefore represents a less onerous starting material which is more readily available in large quantities.

Irrespective of the method of extraction or the vegetable material used, it is important for the reasons mentioned above that the extraction solvent should be as apolar as possible. The extraction solvent will be selected from the solvents typically used as extraction solvents, i.e., solvents of relatively low boiling point, such as saturated, optionally branched hydrocarbons, for example hexane, pentane, heptane, 2-methyl butane, 2-methyl hexane and cyclohexane or mixtures of saturated hydrocarbons (petroleum ethers), or aromatic hydrocarbons such as toluene, or even binary mixtures of one of the above-mentioned solvents in a large excess with a chlorine-containing solvent (for example methylene chloride, chloroform, chloroethylenes) or oxygen-containing solvent, such as an ether (for example diethyl ether), or a ketone (for example acetone) or an ester (for example ethyl acetate) or an alcohol (for example ethanol, methanol, etc.). For example, it is possible to use a mixture of petroleum ethers, toluene or hexane with dichloromethane or ethanol in a ratio of 99:1 to 90:10. In the case of sage for example, the carnosic acid can be quantitatively extracted with a solvent of the saturated hydrocarbon type. With all the other combinations of vegetable material and extraction variant, it will be necessary to use a solvent of slightly increased polarity if a high degree of extraction of carnosic acid is to be obtained.

The step in which the spice is extracted may be carried out either by solvent extraction of the vegetable material, for example in an extractor of the Soxhlet type (variant I) or by charging, i.e., by immersion of the vegetable material in the solvent (variant II), or by percolation or by extraction in a pulsed column or by any other known solvent-based solid extraction technique. However, it is the first two variants that are exemplified in the following. Variant I gives better carnosic acid extraction yields than variant II although variant II is more convenient to use where large quantities of vegetable material have to be extracted.

Extraction by solvent extraction is carried out in an extractor of the Soxhlet type consisting of a reflux apparatus (flask+condenser) which contains the extraction solvent and between the two parts of which is arranged a siphon extractor equipped with a porous cartridge containing the vegetable material to be extracted. The vapours of the solvent heated to the boiling temperature in the flask pass along the extractor into a tube provided for this purpose and condense into liquid form on arrival in the condenser. The condensed solvent drops back into the extraction cartridge which it fills. When the liquid level in the extractor reaches the level of the siphoning tube, the extractor discharges its liquid contents which return to the flask, entraining a certain quantity of dissolved vegetable material. The process as a whole may be defined as an extraction cycle.

In this method of extraction, the preferred solvents for sage are light acyclic hydrocarbons, for example petroleum ether, preferably having a boiling temperature in the range from 40° to 60° C., and for rosemary the same solvents or a binary combination of one of them with a chlorine-containing solvent, for example dichloromethane, in a ratio by volume of 99:1 to 9:1. The number of extraction cycles applied to the material to be extracted is of the order of 5 to 20.

Where extraction is carried out in batches, the vegetable material and the extraction solvent are contacted in a conventional reactor and the mixture is stirred throughout the operation. The proportions of solvent and vegetable material are preferably in a volume/weight ratio of 5:1 in the case of rosemary and 10:1 in the case of sage (the largest quantity of solvent in the case of sage is determined by the much lower mass by volume of sage compared with that of rosemary). Generally, the vegetable material will be subjected to two or three successive extractions, the liquid phase and the solid phase being separated by filtration or centrifugation between each operation. The duration of each extraction is of the order of 30 minutes to 2 hours and generally 1 hour. The preferred solvents in this method of extraction for both the vegetable materials sage and rosemary are aromatic hydrocarbons, preferably toluene, or a binary combination of a light acyclic hydrocarbon, for example petroleum ether or hexane, with an oxygen-containing solvent, preferably ethanol or methanol, in ratios by volume of 99:1 to 9:1.

The first extraction step is carried out at a temperature in the range from 20° to 50° C.

In the second step, the vegetable extract obtained in the first step is treated with a solid adsorbent material. The carnosic acid of the extract is selectively adsorbed onto the solid material and, after the liquid phase has been removed, is recovered in concentrated form by desorption with a pure polar solvent, such as acetone, methanol, ethanol or ethyl acetate, or a mixture of one of these solvents in a large excess with an apolar or weakly polar solvent.

In principle, the liquid extract may be treated with any solid adsorbent material having an affinity, or selectivity, for compounds of this type. A list, by no means complete, of the adsorbent materials which may be used for this purpose has already been given in the foregoing. These materials are essentially those which are typically used in separation techniques based on liquid chromatography.

Among the adsorbent materials of economic interest, polyamide or any similar polymer, such as polyvinyl pyrrolidone, are preferred materials for adsorption of the carnosic acid because they show a remarkable affinity for phenolic compounds (cf. for example "The Flavonoids", Harbone et al., Eds., Chapman and Hall, 1975, Chap. 1, p. 11). In addition, they are chemically inert supports which are in no danger of significantly altering the compounds with which they are contacted.

In practice, the liquid vegetable extract of the first step of the process may be contacted as such with the adsorbent material. If necessary, the extract may be filtered beforehand to remove small quantities of precipitated solid materials which may have formed during or after extraction. In practice, however, it is of advantage to concentrate the liquid extract before it is contacted with the adsorbing agent to promote the passage of the carnosic acid from the dissolved state into the adsorbed state. In numerous cases when the concentration step is accompanied by the formation of a solid precipitate, the solvent is preferably removed completely from the extract and the residue taken up in a second solvent selected for its ability readily and completely to dissolve the carnosic acid of the extract. In practice, it has been found that solvents of the aromatic hydrocarbon or chlorine-containing type are suitable for this operation, toluene and dichloromethane being the preferred solvents.

The liquid extract may be contacted with the adsorbent material by immersion or by passage of the extract through a column filled with the adsorbent material. The second alternative is more effective and may be carried out by introducing the liquid extract at the head of a column filled with the adsorbent material conditioned with the same solvent as that of the extract. When the extract is in contact with the adsorbent material, the column is washed with fresh solvent until all the materials of the extract have been eliminated except for the carnosic acid, which remains adsorbed on the support. The carnosic acid is then desorbed from the adsorbent material by passage through the column of a medium-polarity to polar solvent, for example a mixture of dichloromethane or toluene with ethanol or methanol. The solvent is removed from the eluate and the residue may even be subsequently purified by recrystallization to achieve the desired degree of purity of carnosic acid.

The present invention also relates to the use of carnosic acid for the preparation of a composition or diet intended for the prevention or treatment of cancer.

Certain chemical compounds have properties which, directly or indirectly, reduce or suppress the mutagenic activity induced by other chemical products. Thus, it has been shown that free radicals are capable of inducing a large number of different lesions in DNA and that they are also involved in the process as of cancer, ageing and cardiovascular disease. Carnosic acid has an inhibiting effect on the degradation of DNA caused by the free radicals so that it may be considered for use in the prevention and treatment of cancerous or cardiovascular diseases.

The dietetic or pharmaceutical compositions may be made up in various forms adapted to the method of administration, to a subject, for example oral, enteral or parenteral. For example, they may be made up as capsules, gelatin-coated tablets or syrups. In the case of enteral or parenteral administration, the compositions will be made up in the form of physically and chemically stabilized solutions or emulsions.

Physiological doses may be administered in the prevention or, optionally, the treatment of certain forms of cancer and cardiovascular disease.

In addition, the carnosic acid may be used for the preparation of a composition intended for the treatment of herpes which is a viral disease. This composition may be presented to a subject in various forms adapted to the method of administration, for example oral or topical application. For example, the composition may be presented in the form of capsules, gelatin-coated tablets or ointments. Physiological doses are administered for the treatment of this disease.

EXAMPLES

The invention is illustrated by the following Examples.

EXAMPLES 1 TO 21

Table 1 below illustrates the results obtained from a series of tests on the extraction of rosemary and sage by extraction variants I and II using the solvents described above. It can be seen that the higher the polarity of the solvent (column 5), the better the extraction yield of carnosic acid (column 8), but the lower the concentration of carnosic acid in the extract (column 7) and the larger the amount of ballast in the extract, the ballast being formed in particular by phenolic compounds other than carnosic acid which are therefore capable of interfering negatively with the carnosic acid in the second step of the process.

| 1 Example | 2 Start mat. | 3 Ca content (%) | 4 Extraction variant | 5 Extraction solvent | 6 Extraction yield (%) | 7 CA content in extract (%) | 8 CA extraction yield (%) | 9 QI of extr. (max = 100) |
|---|---|---|---|---|---|---|---|---|
| 1 | Rosemary | 1.85 | I | P | 9.1 | 16 | 79 | 68 |
| 2 | Rosemary | 1.85 | I | P/D 9/1 | 10.1 | 16 | 87 | 76 |
| 3 | Rosemary | 1.85 | I | P/D 9/1 | 11.1 | 15 | 91 | 74 |
| 4 | Sage | 2.50 | I | P | 10.0 | 25 | 100 | 100 |
| 5 | Rosemary | 1.80 | II | P | 5.8 | 13 | 42 | 30 |
| 6 | Rosemary | 1.80 | II | T | 9.6 | 14 | 75 | 58 |
| 7 | Rosemary | 1.80 | II | P/E 98/2 | 8.2 | 16 | 73 | 65 |
| 8 | Rosemary | 1.80 | II | P/E 99/1 | 7.2 | 15 | 60 | 50 |
| 9 | Rosemary | 1.80 | II | P/E 98/2 | 8.2 | 15 | 68 | 57 |
| 10 | Rosemary | 1.80 | II | P/E 95/5 | 11.4 | 13 | 82 | 59 |
| 11 | Rosemary | 1.80 | II | P/A 98/2 | 6.4 | 13 | 46 | 33 |
| 12 | Rosemary | 1.80 | II | P/A 95/5 | 7.6 | 14 | 59 | 46 |
| 13 | Rosemary | 1.80 | II | P/A 9/1 | 10.0 | 12 | 67 | 44 |
| 14 | Sage | 1.80 | II | P | 6.0 | 16 | 53 | 47 |
| 15 | Sage | 1.80 | II | P/E 99/1 | 9.0 | 15 | 75 | 63 |
| 16 | Sage | 1.80 | II | P/E 98/2 | 9.0 | 15 | 75 | 63 |
| 17 | Sage | 1.80 | II | P/E 95/5 | 13.4 | 11 | 82 | 50 |
| 18 | Sage | 1.80 | II | T | 10.2 | 16 | 91 | 82 |
| 19 | Sage | 1.80 | II | P/A 98/2 | 6.8 | 14 | 53 | 41 |
| 20 | Sage | 1.80 | II | P/A 95/5 | 8.4 | 16 | 75 | 66 |
| 21 | Sage | 1.80 | II | P/A 9/1 | 11.6 | 13 | 84 | 61 |

Legend:
CA: Carnosic acid
QI: Quality index
Solvents:
P = petroleum ether
E = ethanol
A = acetone
D = dichloromethane
T = toluene On the basis of the measured data set out in the Table, it is possible to define a quality index (QI) of the extract which is determined from the criteria of effectiveness and selectivity of the extraction solvent. The effectiveness (E) of the solvent is measured by the degree of extraction of the carnosic acid (column 8). The more effective the solvent, the better will be the yield of carnosic acid recovered at the end of the process. The selectivity (S) of the extraction solvent is measured by the content of carnosic acid in the extract (column 7). The more selective the solvent, the better will be the purity of the carnosic acid isolated at the end of the process. The quality index (QI) may thus be defined as the product of the factors E and S weighted by the content of carnosic acid (T) in the vegetable starting material (column 3).

$$QI = (E \times S) / T$$

To facilitate comparison of the various examples in Table 1, the quality index (column 9) was relativized to a scale of 100, the data of Example 4 being arbitrarily considered as optimal.

Examination of the data in the Table enables the following observations to be made:

1) The quality index is the expression of a compromise between selectivity and effectiveness. The ideal solvent would be that which extracted all, and only, the active material required. The compromise to be made is to find a balance between the yield of the process for obtaining the active material and the economy of that process.

2) Given a comparable extraction variant and solvent, the carnosic acid is extracted more easily from sage than from rosemary.

3) Given a comparable solvent and irrespective of the vegetable starting material, extraction variant I is more effective than variant II.

4) The use of binary mixtures of extraction solvents with an increasing proportion of the more polar solvent enables an optimal concentration of the more polar solvent to be defined. This optimal concentration is around 5% in the case of the Examples given in the Table (Examples 7-9, 10-12, 15-17, 18-19).

Specific examples of the extraction of carnosic acid in accordance with the Examples 4, 1, 2, 7 and 18 of Table 1 above are given in the following.

SAGE, EXTRACTION VARIANT I, EXAMPLE 4

297 g ground officinal sage containing 2.5% carnosic acid are introduced into an extractor of the Soxhlet type equipped with a cellulose cartridge. The sage is extracted with petroleum ether (2.5 l; Bp. 40°–60° C.) for 48 h in the absence of air (nitrogen atmosphere). On completion of extraction, the solvent is removed in a rotary evaporator and 30 g of a coloured oily extract (yield 10%) containing 7.4 g carnosic acid (yield 100%) are collected.

The extract is dissolved in dichloromethane (150 ml), and after this solution has been filtered to eliminate a small proportion of insoluble material, the solution is poured into a column filled with polyamide and prepared from a suspension of 150 g of that material in 1 l dichloromethane. The column is then eluted with the same solvent to eliminate those materials from the extract which are not retained on the polyamide and which correspond to a strongly coloured fraction (fraction 1, 7 ml, 18 g residue without solvent). Elution is continued with an 8:2 (v/v) of dichloromethane and methanol. The transition zone between the two solvents shows up on the column in the form of a ring-shaped yellow zone which corresponds to the carnosic acid. An intermediate fraction (fraction 2, 700 ml, 2 g residue without solvent) and then the ring zone (fraction 3, 100 ml, 6.1 g residue after removal of the solvent) are collected.

After trituration in petroleum ether, the semi-crystalline residue of fraction 3 gives 6.0 g of a light yellow solid (Mp. 170°–195° C.) containing 95% carnosic acid. Yield: 82%.

ROSEMARY, EXTRACTION VARIANT I, EXAMPLE 1

A stocking of thin cloth containing 383 g ground rosemary containing 1.85% by weight carnosic acid is placed in the extraction container of a Soxhlet extractor. The height of the vegetable mass in the extractor measures 30 cm. The extractor is placed under an inert atmosphere and the rosemary is extracted with petroleum ether (2.5 l; Bp. 40°–60° C.) in a total of 4 filling and siphoning cycles each lasting 75 minutes. The solvent is removed in a rotary evaporator and 35 g of a dark oily extract (yield 9.1%) containing 5.6 g carnosic acid (yield 79%) are collected.

The extract is dissolved in 240 ml dichloromethane and the solution is poured onto a column of polyamide. The column is eluted in the same way as before, 3 fractions being collected, namely: fraction 1, 700 ml; fraction 2, 550 ml; fraction 3, 50 ml.

The solvent is removed from the last fraction and 7.3 g of a deep yellow solid mass containing 5.6 g (77%) carnosic acid, i.e., the entire extracted fraction of that acid, are obtained. Yield: 79%.

ROSEMARY, EXTRACTION VARIANT I, EXAMPLE 2

The procedure is as in the preceding Example, except that the rosemary is extracted with a 9/1 (v/v) mixture of petroleum ether and dichloromethane. The extract weighs 38 g (yield 10.1%) and contains 6.2 g carnosic acid (yield 87%). Part of the extract (4 g) is insoluble in dichloromethane and care has to be taken to filter this solid material before applying the extract to the column of polyamide. The residue of fraction 3 obtained by elution weighs 7.7 g and contains 5.3 g (59%) carnosic acid. Yield: 74%.

ROSEMARY, EXTRACTION VARIANT II, EXAMPLE 7

2.5 kg ground rosemary containing 1.8% carnosic acid and 12.5 l of a 98/2 (v/v) mixture of hexane and ethanol are introduced into a 20 liter reactor. The whole is stirred for 1 hour at ambient temperature in a nitrogen atmosphere. The liquid phase is separated from the solid phase by vacuum filtration (Büchner). The solution of the extract is placed on one side and the vegetable mass is subjected to a second extraction similar to the first. After filtration, the two extract solutions are combined and the solvent is removed in a rotary evaporator. 206 g (yield 8.2%) of a dark oily extract containing 33 g carnosic acid (yield 73%) are obtained.

The extract is dissolved in 1.6 l dichloromethane and the solution is poured onto a column of polyamide. The column is eluted as in Example 1, 3 fractions being collected, namely: fraction 1, 3.36 l; fraction 2, 3.23 l; fraction 3, 1.65 l. After evaporation of the solvent, the last fraction gives a semi-oily residue (41.5 g) which is triturated in petroleum ether to a solid consistency. The yellow product thus obtained weighs 37 g and contains 73% carnosic acid. Yield: 27 g (60%).

SAGE, EXTRACTION VARIANT II, EXAMPLE 18

A mixture of 50 g ground sage (carnosic acid content 1.8%) and 600 ml toluene is stirred for 1 hour at ambient temperature in a nitrogen atmosphere. After separation of the two phases (solid and liquid) by filtration, the vegetable mass is subjected to a second extraction. The 2 extract solutions are combined and the solvent is removed in a rotary evaporator. 5.1 g (10.2%) of an oily residue containing 0.82 g carnosic acid (yield 91%) are obtained.

The extract is redissolved in 50 ml toluene and the solution obtained is filtered to eliminate some insoluble materials. The filtrate is poured onto a column of polyamide (30 g; 30×2 cm) conditioned in toluene. The column is eluted as in Example 1 with toluene and then with an 8/2 mixture of toluene and ethanol, 3 fractions being collected, namely: fraction 1, 200 ml (3.3 g vegetable matter); fraction 2, 160 ml (0.2 g); fraction 3, 50 ml (1.1 g). The last fraction contains 0.78 g (71%) carnosic acid. Yield: 87%.

PURIFICATION OF THE CARNOSIC ACID 30 g of the yellow product obtained in Example 7 containing 73% carnosic acid are recrystallized twice in cyclohexane in the presence of active charcoal. 16.4 g carnosic acid are obtained in the form of colourless crystals with a purity of more than 95% (melting point: 193°–199° C.). Instead of cyclohexane, the product may also be recrystallized from benzene or toluene.

The physiological anticarcinogenic and antiviral properties of carnosic acid are illustrated in the following tests:

ANTICARCINOGENIC ACTIVITY OF CARNOSIC ACID

The antimutagenic activity of carnosic acid was evaluated in an Ames test using the strain Salmonella typhimurium TA 102 which is known to respond readily to active oxygen-containing species. This strain is placed in tert. butyl peroxide (tBOOH) which is known to produce peroxyl radicals and of which the biological action is considered to be particularly interesting because it generates the oxygen radicals inside the cells. The tBOOH produces a certain number of local alterations in the DNA of the bacteria and the inhibition of these alterations produced by the antioxidant when it is incorporated in the culture medium is measured. The following antioxidants were tested in a range of active doses: carnosic acid, carnosol and ascorbic acid. The ascorbic acid, of which the anticarcinogenic activity is well known, served as a positive control. In order to dissociate the "true" antimutagenic effect from a bactericidal effect, a pre-incubation test is used and the results are expressed in the form of the ratio: number of revertant colonies induced/number of surviving colonies [Aeschbacher et al., Food Safety, 8, 167–177 (1987)].

Description of the test: the incubation medium is prepared by mixing 1 ml bacterial suspension ($5 \times 10^9$ bact./ml) of Salmonella typhimurium TA 102 prepared in accordance with Maron and Ames [Mutation Research, 113, 175–215 (1983)], 50 μl saline buffer, 0.95 ml 0.15M KCl ad 2.8 ml Davis-Mingioli medium supplemented with 24 μg histidine and 10 μg biotine per ml. 0.5 ml tBOOH solution (final concentration 2.5 mM) and 0.5 ml of a solution of antioxidant in water for the ascorbic acid and in medium-chain triglycerides for the water-insoluble antioxidants, carnosic acid and carnosol, are then added. The medium is incubated for 1 hour at 37° C. and, after addition of 9 ml 0.8% nutrient broth, for another 3 hours at 37° C. to fix the mutation. The medium is then centrifuged and the washed bacteria are resuspended in 3.5 ml saline buffer.

Counting of the revertant and surviving colonies is carried out on plates of nutrient agar, which have been incubated for 3 days at 37° C. and to which 0.1 ml of the above bacterial suspension has been applied, respectively in the absence and presence of histidine. Counting is carried out automatically using a Fisher Count-All 800 counter.

Table 2 expresses the results obtained in the form of the estimated concentrations of antioxidants tested which are capable of reducing by half the mutagenic effect induced by the tBOOH in a concentration of 2.5 mM in the absence of antioxidants (inhibiting concentration 50 = IC 50).

TABLE 2

| Input | Compound | IC50 (mg) | IC50 (mM) | Relative activity, comparison of the IC50 (mM) |
|---|---|---|---|---|
| 1 | Carnosic acid | 0.3 | 0.15 | 100 |
| 2 | Carnosol | 17.8 | 9.3 | 2 |
| 3 | Ascorbic acid | 2.8 | 2.7 | 6 |

It is clearly apparent from the results set out in the Table that, although the anticarcinogenic activity of carnosol is slightly weaker, but of an order comparable with that of ascorbic acid (positive control), the activity of carnosic acid is higher by a factor of approximately 15 than that of ascorbic acid and by a factor of 50 than that of carnosol.

Antiviral Activity of Carnosic Acid

The antiviral activity of carnosic acid was tested in vitro at various concentrations (5; 2.5; 1.25; 0.62 μg/ml) against infectious batches of simple herpes of type 1 (HSV1) and type 2 (HSV2) and of polio virus of type 3 (polio 3) cultured on the VERO cell line. After incubation for 2 hours, the titers obtained are compared with that of the inhibitor-free controls (test 1). Aliquot portions of various test supernatants are then inoculated onto new cells. After incubation for 4 days, counting of the viral particles this time enables viral production in the presence of the inhibitor to be evaluated (test 2). The results of these two tests are set out in Table 3 below.

TABLE 3

Concentration Number of viral particles/0.025 ml supernatant of carnosic acid

| (μg/ml) | Test 1 | | | Test 2 | | |
|---|---|---|---|---|---|---|
| | HSV1 | HSV2 | POLIO 3 | HSV1 | HSV2 | POLIO 3 |
| 5 | 10 | 10 | $10^{12}$ | $10^2$ | <10 | $2 \times 10^{23}$ |
| 2.5 | 10 | 10 | $10^{12}$ | $10^5$ | $2 \times 10^2$ | $2 \times 10^{23}$ |
| 1.25 | $10^3$ | 10 | $10^{12}$ | $2.5 \times 10^6$ | $10^5$ | $10^{23}$ |
| 0.62 | $10^4$ | 10 | $10^{12}$ | $6 \times 10^6$ | $8 \times 10^5$ | $10^{22}$ |
| 0 (control) | $10^5$ | $10^4$ | $10^{12}$ | $2 \times 10^8$ | $10^7$ | $10^{23}$ |

The results of test 1 show that the virus strain polio 3 is not inhibited by carnosic acid. By contrast, the anti-HSV1 and anti-HSV2 effect is altogether significant because reductions in titer of as much as 3 to 4 factors of 10 are observed. Carnosic acid therefore has a specific effect. The results of test 1 are confirmed by those of test 2. It is found that the production of polio 3 can be considered as equivalent, irrespective of the concentration of carnosic acid. By contrast, the production of HSV1 and HSV2 is greatly affected. This confirms the specificity of the effect of the product and also the absence of cell toxicity because, at the highest concentration (5 μg/ml), there is no change in the production of polio 3.

We claim:

1. A process for obtaining carnosic acid comprising extracting a vegetable material selected from the group consisting of sage and rosemary with an apolar solvent to obtain an extract containing apolar compounds including carnosic acid, contacting the extract with an adsorbent material having an affinity for polar compounds for adsorbing the carnosic acid to separate the carnosic acid from the apolar compounds of the extract, desorbing the adsorbent material with a polar solvent to obtain the carnosic acid in the solvent and then evaporating the polar solvent from the carnosic acid to obtain a residue containing the carnosic acid.

2. A process according to claim 1 further comprising crystallizing the carnosic acid from the residue.

3. A process according to claim 1 further comprising triturating the residue in petroleum ether.

4. A process according to claim 1 further comprising triturating the residue in petroleum ether and then crystallizing the carnosic acid from the residue.

5. A process according to claim 1 or 2 or 3 further comprising concentrating the extract to obtain a concentrated extract and then contacting the concentrated extract with the adsorbent material.

6. A process according to claim 1 further comprising concentrating the extract, and wherein a precipitate is formed during concentration, further comprising adding a solvent to the precipitate to dissolve the carnosic acid and then contacting the solvent with the adsorbent material.

7. A process according to claim 6 wherein the precipitate dissolving solvent is selected from the group consisting of an aromatic hydrocarbon and a chlorine-containing hydrocarbon.

8. A process according to claim 6 wherein the solvent is selected from the group consisting of toluene and dichloromethane.

9. A process according to claim 1 wherein the vegetable material is extracted at a temperature of from 20° C. to 50° C.

10. A process according to claim 1 wherein the adsorbent material is contained in a column and wherein the extract is contacted with the adsorbent material by passing the extract through the material in the column.

11. A process according to claim 1 wherein the apolar solvent is selected from the group consisting of saturated hydrocarbon solvents and aromatic hydrocarbon solvents and mixtures thereof.

12. A process according to claim 11 wherein the apolar solvent further comprises a solvent selected from the group consisting of a chlorine-containing solvent, an ether solvent, a ketone solvent, an ester solvent and an alcohol solvent.

13. A process according to claim 1 wherein the apolar solvent is an acyclic hydrocarbon having a boiling point of from 40° C. to 60° C.

14. A process according to claim 1 wherein the vegetable material is rosemary and the apolar solvent further comprises a chlorine-containing solvent in a ratio of acyclic hydrocarbon to chlorine-containing solvent of from 99:1 to 90:10.

15. A process according to claim 14 wherein the chlorine-containing solvent is dichloromethane.

16. A process according to claim 1 wherein the apolar solvent is selected from the group consisting of pentane, hexane, heptane, 2-methylbutane, 2-methylhexane, cyclohexane, and toluene and mixtures thereof.

17. A process according to claim 16 wherein the apolar solvent further comprises a solvent selected from the group consisting of methylene chloride, chloroform, chloroethylenes, dichloromethane, ether, diethyl ether, acetone, ethyl acetate, methanol and ethanol.

18. A process according to claim 1 wherein the apolar solvent is selected from a group of saturated hydrocarbon solvents consisting of petroleum ethers, toluene and hexane in combination with a further solvent selected from the group consisting of dichloromethane and ethanol, wherein the ratio of the saturated hydrocarbon solvent to further solvent of from 99:1 to 90:10.

19. A process according to clam 1 wherein the adsorbent is selected from the group consisting of silica gel, aluminum oxide, polyamide and polyvinyl pyrrolidone.

20. A process according to claim 1 wherein the polar solvent is selected from the group consisting of methanol, ethanol, acetone and ethyl acetate.

21. A process according to claim 1 wherein the polar solvent is selected from the group consisting of methanol and ethanol in admixture with a further solvent selected from the group consisting of dichloromethane and toluene.

* * * * *

UNITED STATES PATENT AND TRADEMARK OFFICE
CERTIFICATE OF CORRECTION

PATENT NO.   : 5,256,700
DATED        : October 26, 1993
INVENTOR(S)  : Robert AESCHBACH, et al.

It is certified that error appears in the above-identified patent and that said Letters Patent is hereby corrected as shown below:

Column 2, line 53, "obtained" should be --obtaining--.

Column 2, line 55, delete "highly".

Column 3, line 25, insert a comma after "selectivity".

Column 6, line 43, delete "process as" and insert therefor --processes--.

Column 12, line 49 (line 1 of claim 5), "3" should be --4--.

Column 14, line 15 (line 1 of claim 19), "clam" should be --claim--.

Signed and Sealed this

Ninth Day of May, 1995

Attest:

BRUCE LEHMAN

*Attesting Officer*   *Commissioner of Patents and Trademarks*